United States Patent
Srinivasan et al.

(10) Patent No.: US 11,076,834 B2
(45) Date of Patent: Aug. 3, 2021

(54) COMMON MODE NOISE SUPPRESSION USING CHANNEL DATA PROCESSING

(71) Applicant: EDAN INSTRUMENTS, INC., Shenzhen (CN)

(72) Inventors: Seshadri Srinivasan, Sunnyvale, CA (US); Yang Peng, Sunnyvale, CA (US); Yonggang Dong, Sunnyvale, CA (US); Sean Murphy, Sunnyvale, CA (US); Jianhua Mo, Sunnyvale, CA (US)

(73) Assignee: EDAN INSTRUMENTS, INC., Shenzhen (CN)

( * ) Notice: Subject to any disclaimer, the term of this patent is extended or adjusted under 35 U.S.C. 154(b) by 964 days.

(21) Appl. No.: 14/973,634

(22) Filed: Dec. 17, 2015

(65) Prior Publication Data

US 2017/0071578 A1    Mar. 16, 2017

(30) Foreign Application Priority Data

Sep. 11, 2015 (CN) .......................... 201510577269.0

(51) Int. Cl.
*A61B 8/08* (2006.01)
*A61B 8/00* (2006.01)
*G01S 7/52* (2006.01)

(52) U.S. Cl.
CPC .......... *A61B 8/5269* (2013.01); *A61B 8/4427* (2013.01); *A61B 8/5207* (2013.01);
(Continued)

(58) Field of Classification Search
CPC ............. G01S 7/52077; G01S 7/52046; G01S 7/52082; A61B 8/5207; A61B 8/54; H04B 1/7174; H04B 1/00
See application file for complete search history.

(56) References Cited

U.S. PATENT DOCUMENTS 4,984,465 A  *  1/1991  Piel, Jr. ................ G01S 7/52077
                                                        73/602
6,636,573 B2 * 10/2003  Richards .................... H03L 7/18
                                                        375/355
(Continued)

FOREIGN PATENT DOCUMENTS

CN      101416886 A      4/2009
CN      101452678 A      8/2009
(Continued)

OTHER PUBLICATIONS

Shem-Tov et al. 2004 Proc. IEEE ICECS 2004 p. 113-116 (Year: 2004).*

(Continued)

*Primary Examiner* — Michael J Tsai
*Assistant Examiner* — Patrick M Mehl

(57) ABSTRACT

An ultrasound processing system includes an ultrasound interface and processing electronics. The ultrasound interface receives imaging information. The processing electronics are coupled to the ultrasound interface and are configured to perform processing across a plurality of ultrasound channels by combining channel data for adaptively reducing the common mode noise prior to beamforming for a transmit event. The combination of the channel data may be computing an arithmetic mean, which is then multiplied to a weighting coefficient. This value may then be removed from the individual channel data. The modified channel data is then transmitted to a beamformer, which processes the channel data for directional signal transmission and reception.

11 Claims, 6 Drawing Sheets

(52) U.S. Cl.
CPC ...... *G01S 7/52046* (2013.01); *G01S 7/52077* (2013.01); *A61B 8/54* (2013.01); *G01S 7/52082* (2013.01)

(56) References Cited

U.S. PATENT DOCUMENTS

| | | | | |
|---|---|---|---|---|
| 6,685,645 | B1* | 2/2004 | McLaughlin | A61B 8/08 600/447 |
| 7,957,609 | B2* | 6/2011 | Lu | G01S 7/52046 345/643 |
| 2003/0231125 | A1* | 12/2003 | Freeman | G01S 7/52028 341/143 |
| 2007/0236374 | A1* | 10/2007 | Brueske | G01S 7/52028 341/143 |
| 2009/0036772 | A1* | 2/2009 | Lu | G01S 7/52046 600/437 |
| 2009/0110033 | A1* | 4/2009 | Shattil | H04B 1/7174 375/141 |
| 2011/0015532 | A1* | 1/2011 | Koertge | A61B 5/0402 600/509 |
| 2013/0116561 | A1* | 5/2013 | Rothberg | A61B 8/4494 600/438 |
| 2014/0180105 | A1 | 6/2014 | Hancock et al. | |

FOREIGN PATENT DOCUMENTS

| | | |
|---|---|---|
| CN | 102262490 A | 11/2011 |
| CN | 103135875 A | 6/2013 |
| CN | 103961094 A | 8/2014 |

OTHER PUBLICATIONS

ST Microelectronics 2014 Application Note AN4511 Common mode filters, 21 pages; initial release date Jul. 29, 2014 (Year: 2014).*
Kortbeck et al 2013 Ultrasonics 53:1-16 (Year: 2013).*
Chinese First office action,Chinese Application No. 201510577269.0, dated Aug. 25, 2017(8 pages).
Chinese second office action,Chinese Application No. 201510577269.0, dated Nov. 4, 2018(7 pages).
Chinese third office action,Chinese Application No. 201510577269.0, dated Oct. 25, 2018(7 pages).
Chinese fourth office action,Chinese Application No. 201510577269.0, dated Nov. 25, 2019(10 pages).
Notication of grant of patent right for invention,Chinese Application No. 201510577269.0, dated Mar. 3, 2020(3 pages).
Research on EHG signal picking and data processing,Wei Jiang,2002.

* cited by examiner

COMMON MODE NOISE SUPPRESSION USING CHANNEL DATA PROCESSING

CROSS-REFERENCE TO RELATED APPLICATION

This application claims priority from Chinese Patent Application No. 201510577269.0, filed Sep. 11, 2015. The contents of this application is incorporated herein by reference in its entirety.

BACKGROUND

The present invention relates generally to ultrasound systems that include processing electronics. More specifically, the present invention relates to a channel data processor that combines channel data prior to beamforming for common mode noise suppression.

Ultrasound systems can experience common mode noise arising from the clock frequency of the DC power supply, or other sources of high frequency interference. This common mode noise can appear in the ultrasound images created, decreasing the quality of the images. This decrease in quality can lead to images that are harder to read, and could lead to misdiagnosis.

Conventional ultrasound imaging systems acquire channel data and perform beamforming as the first step with minimal channel data processing. Typically downsampling and demodulation are done on the channel data prior to beamforming. Such systems rely on sophisticated analog filtering in transmit and receive and expensive grounding mechanisms to reduce external noise.

The inventors of the present invention have recognized that the conventional ultrasound systems techniques fail to suppress common mode noise prior to beamforming. It would be desirable to have processing electronics to suppress the common mode noise using channel data processing techniques prior to beamforming. These techniques may include combining channel data. The benefits of these processing electronics include lower interference noise from external sources, improved tolerance to variations in the analog ultrasound components and transducers, improved imaging modes especially the Doppler modes, and reduced system cost.

SUMMARY OF THE INVENTION

One implementation of the present disclosure of the invention relates to an ultrasound processing system. The ultrasound system includes an ultrasound interface that receives ultrasound imaging information. The ultrasound system further includes processing electronics coupled to the ultrasound interface and configured to utilize the ultrasound imaging information to perform processing across a plurality of ultrasound channels by combining channel data for adaptively reducing the common mode noise prior to beamforming for a transmit event.

In some embodiments, the processing electronics of the ultrasound processing system combine the ultrasound channel data by obtaining an arithmetic mean.

In some embodiments, the processing electronics of the ultrasound processing system combine the channel data adaptively as a function of time of a transmit event, depth of a spatial dimension in range, and/or a channel of spatial dimension in azimuth.

In some embodiments, the processing electronics of the ultrasound processing system multiply the combined channel data by a weighting coefficient.

In some embodiments, the weighting coefficients change adaptively based on the ultrasound channel data, providing adaptive noise reduction.

In some embodiments, the weighting coefficients are based on spatial distribution.

In some embodiments, the weighting coefficients vary based on the spatial location.

In some embodiments, the weighting coefficients are obtained through reference in a lookup table.

In some embodiments, the weighting coefficient is based on a function of combined elements.

In some embodiments, the combined channel data multiplied by the weighting coefficient is removed from the ultrasound channel data, resulting in modified channel data.

In some embodiments, the modified channel data is achieved by subtraction, for additive noise, or division, for multiplicative noise, of the combined channel data multiplied by the weighting coefficient from the ultrasound channel data.

In some embodiments, prior data processing results are used to determine which channel(s) to eliminate from use.

Another implementation of the present disclosure is an ultrasound machine. The ultrasound machine includes an ultrasound engine configured to receive ultrasound returns representative of an ultrasound scene for display. The ultrasound system further includes an ultrasound processor configured to combine channel data prior to beamforming, wherein the ultrasound processor causes a display output to be generated after processing the combined channel data.

Another implementation of the present disclosure is a method of common mode noise suppression using channel data processing. The method includes receiving ultrasound channel data for a plurality of channels by combining channel data, processing the ultrasound channel data for the plurality of channels, performing beamforming and repeating this process for selected transmit events.

In some embodiments, the second step of the method includes combining the plurality of channels by computing an arithmetic mean.

In some embodiments, the second step of the method includes multiplying the arithmetic mean by a weighting coefficient.

In some embodiments, the second step of the method includes removing the arithmetic mean multiplied by the weighting coefficient from the ultrasound channel data, resulting in modified channel data.

In some embodiments, the second step of the method includes modifying the channel data by subtraction, for additive noise, or division, for multiplicative noise, of the combined channel data multiplied by the weighting coefficient from the ultrasound channel data.

DETAILED DESCRIPTION

Referring generally to the FIGURES, systems and methods for channel data processing are shown, according to various exemplary embodiments. The systems and methods described herein may be used to suppress common mode noise in an imaging system prior to beamforming. For example, the channel data processing may include combining channel data from an ultrasound system prior to beamforming.

The present invention generally relates to systems and methods for adaptively suppressing common mode noise prior to beamforming in an ultrasound system using channel data processing. A channel data processor is used as an example in the various figures to help illustrate the present invention. However, it should be recognized that the present invention can be applied to a wide variety of processing electronics and other electronic devices that process imaging data.

In one embodiment of the present invention, an ultrasound system includes a channel data processor configured to combine channel data (e.g. calculating a mean of the channel data) from a plurality of channels. The processing electronics may be placed to process the channel data prior to beamforming. The processing electronics may be configured to apply a weighting coefficient to the combined channel data. The processing electronics may be further configured to remove the combined channel data from the individual channel data. The common mode noise would then be suppressed, resulting in ultrasound images with less common mode noise.

Figure 1A:
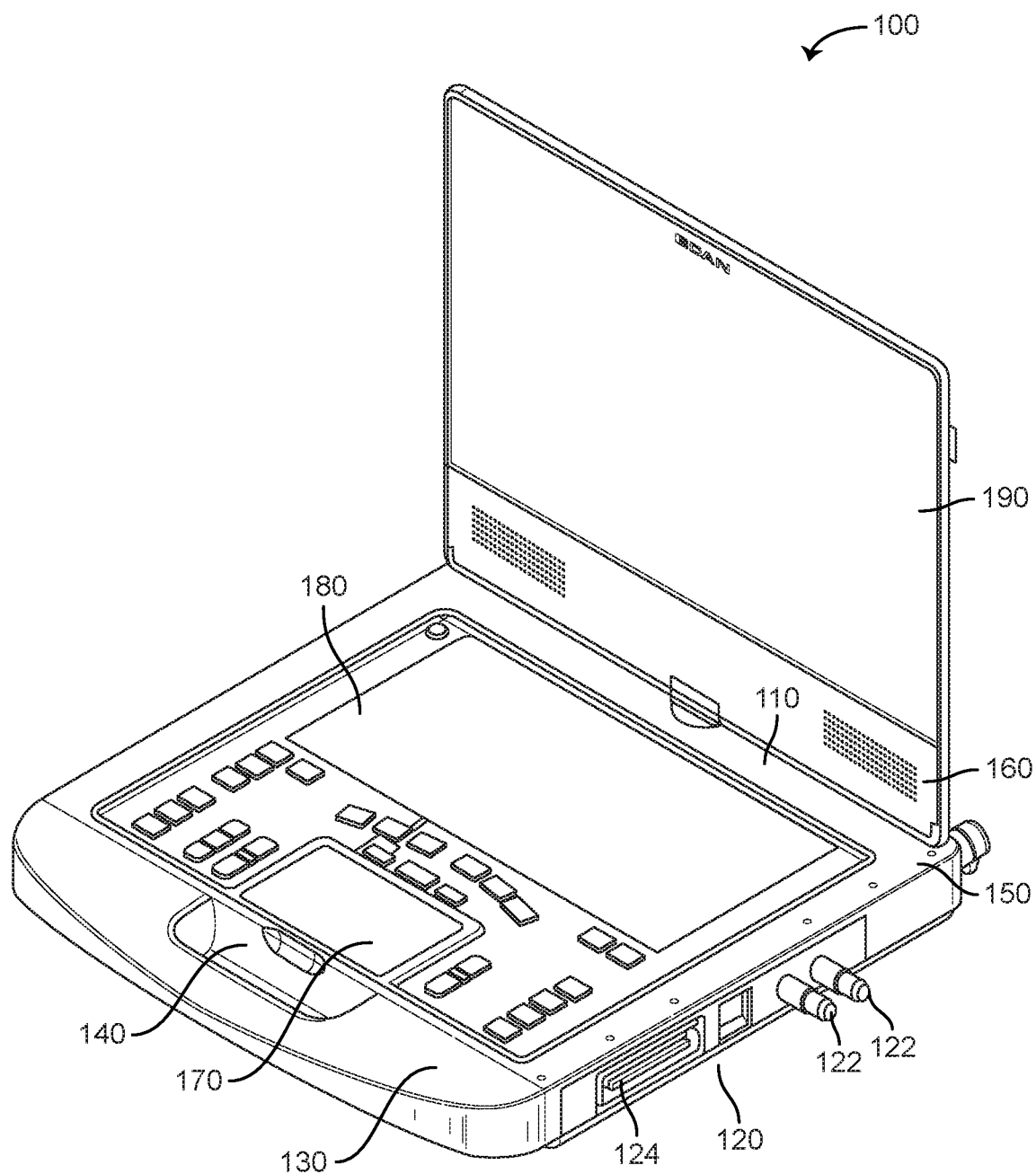
FIG. 1A is a drawing of a portable ultrasound system, according to an exemplary embodiment.

Referring now to FIG. 1A, one embodiment of portable ultrasound system 100 is illustrated. Portable ultrasound system 100 may include display support system 110 for increasing the durability of the display system. Portable ultrasound system 100 may further include locking lever system 120 for securing ultrasound probes and/or transducers. Some embodiments of portable ultrasound system 100 include ergonomic handle system 130 for increasing portability and usability. Further embodiments include status indicator system 140 which displays, to a user, information relevant to portable ultrasound system 100. Portable ultrasound system 100 may further include features such as an easy to operate and customizable user interface, adjustable feet, a backup battery, modular construction, cooling systems, etc.

Still referring to FIG. 1A, main housing 150 houses components of portable ultrasound system 100. In some embodiments, the components housed within main housing 150 include locking lever system 120, ergonomic handle system 130, and status indicator system 140. Main housing 150 may also be configured to support electronics modules which may be replaced and/or upgraded due to the modular construction of portable ultrasound system 100. In some embodiments, portable ultrasound system 100 includes display housing 160. Display housing 160 may include display support system 110. In some embodiments, portable ultrasound system 100 includes touchpad 170 for receiving user inputs and displaying information, touchscreen 180 for receiving user inputs and displaying information, and main screen 190 for displaying information.

Figure 1B:
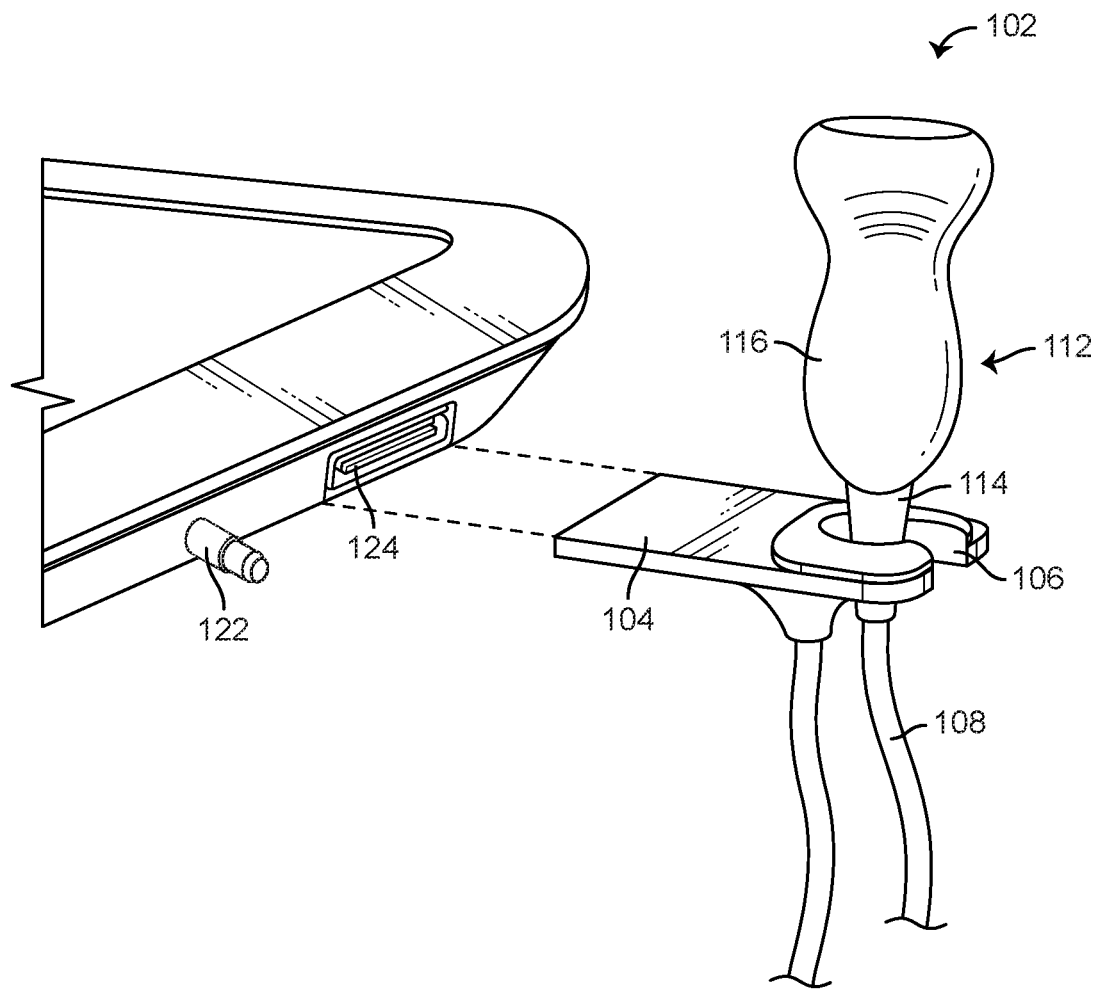
FIG. 1B is a drawing of an ultrasound transducer assembly for coupling to the portable ultrasound system of FIG. 1A, according to an exemplary embodiment.

Referring now to FIG. 1B, ultrasound transducer assembly 102 is shown. According to an exemplary embodiment, ultrasound transducer assembly 102 includes a connection assembly to pin (122) or socket (124) type ultrasound interface, shown as ultrasound interface connector 104, coupled to a cable 108. Cable 108 may be coupled to a transducer probe 112. While FIG. 1B shows only one transducer assembly 102, more transducer assemblies may be coupled to the ultrasound system 100 based on the quantity of pin (122) or socket (124) type ultrasound interfaces.

Ultrasound interface connector 104 is movable between a removed position with respect to pin (122) or socket (124) type ultrasound interface, in which ultrasound interface connector 104 is not received by pin (122) or socket (124) type ultrasound interface, a partially connected position, in which ultrasound interface connector 104 is partially received by pin (122) or socket (124) type ultrasound interface, and a fully engaged position, in which ultrasound interface connector 104 is fully received by pin (122) or socket (124) type ultrasound interface in a manner that electrically couples transducer probe 112 to ultrasound system 100. In an exemplary embodiment, pin (122) or socket (124) type ultrasound interface may include a sensor or switch that detects the presence of the ultrasound interface connector 104.

In various exemplary embodiments contained herein, the ultrasound interface connector 104 may house passive or active electronic circuits for affecting the performance of the connected transducers. For example, in some embodiments the transducer assembly 102 may include filtering circuitry, processing circuitry, amplifiers, transformers, capacitors, batteries, failsafe circuits, or other electronics which may customize or facilitate the performance of the transducer and/or the overall ultrasound machine. In an exemplary embodiment, ultrasound interface connector 104 may include a bracket 106, where the transducer probe 112 may be stored when not in use.

Transducer probe 112 transmits and receives ultrasound signals that interact with the patient during the diagnostic ultrasound examination. The transducer probe 112 includes a first end 114 and a second end 116. The first end 114 of the transducer probe 112 may be coupled to cable 108. The first end 114 of the transducer probe 112 may vary in shape to properly facilitate the cable 108 and the second end 116. The second end 116 of the transducer probe 174 may vary in shape and size to facilitate the conduction of different types of ultrasound examinations. These first end 114 and second end 116 of transducer probe 112 variations may allow for better examination methods (e.g., contact, position, location, etc.).

A user (e.g., a sonographer, an ultrasound technologist, etc.) may remove a transducer probe 112 from a bracket 106 located on ultrasound interface connector 104, position transducer probe 112, and interact with control panel 190 to conduct the diagnostic ultrasound examination. Conducting the diagnostic ultrasound examination may include pressing transducer probe 112 against the patient's body or placing a variation of transducer probe 112 into the patient. The ultrasound image acquired may be viewed on main screen 190.

Figure 2:
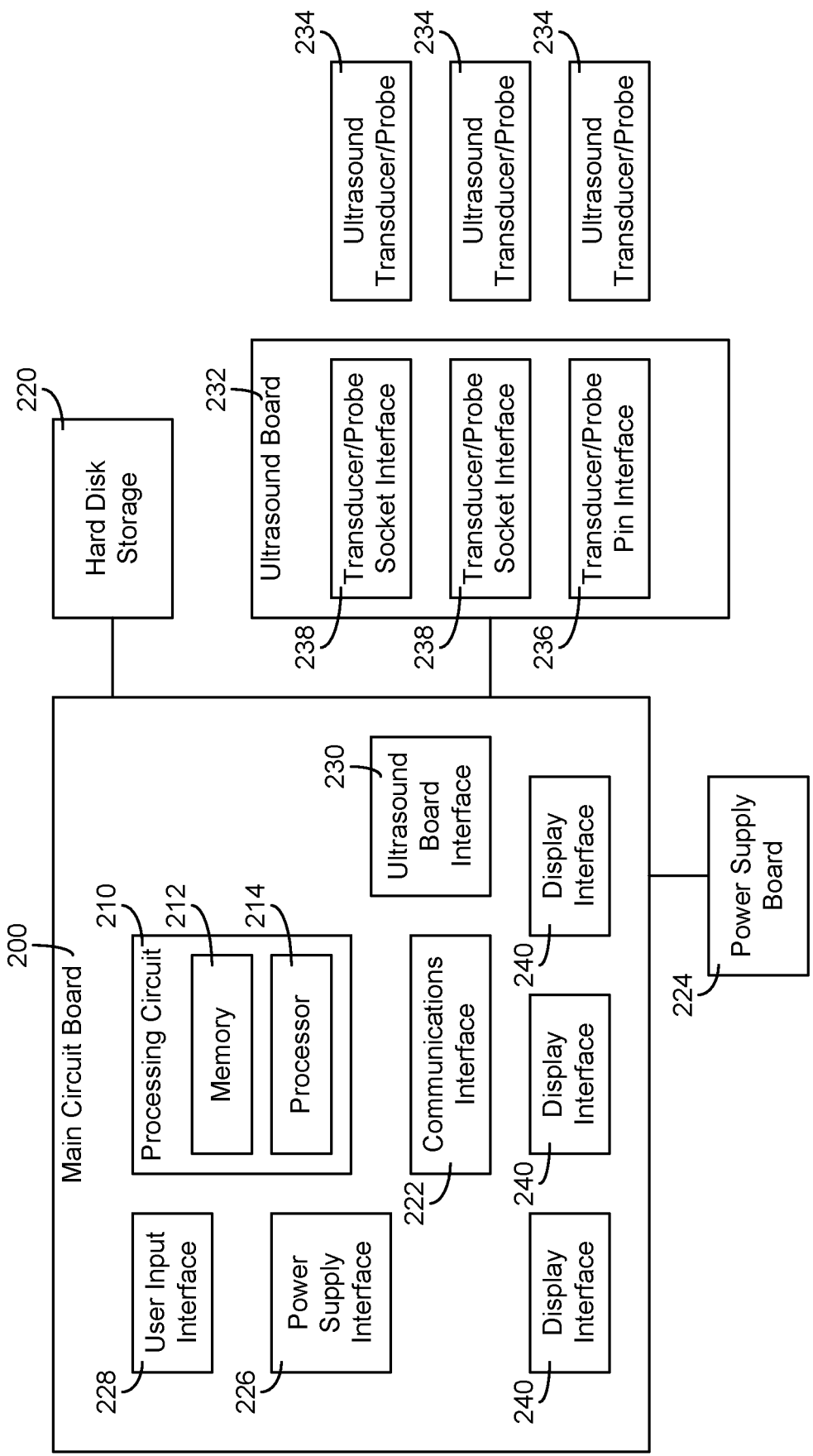
FIG. 2 is a block diagram illustrating components of one embodiment of a portable ultrasound system.

Referring to FIG. 2, a block diagram shows internal components of one embodiment of portable ultrasound system 100. Portable ultrasound system 100 includes main circuit board 200. Main circuit board 200 carries out computing tasks to support the functions of portable ultrasound system 100 and provides connection and communication between various components of portable ultrasound system 100. In some embodiments, main circuit board 200 is configured so as to be a replaceable and/or upgradable module.

To perform computational, control, and/or communication tasks, main circuit board 200 includes processing circuit 210. Processing circuit 210 is configured to perform general processing and to perform processing and computational tasks associated with specific functions of portable ultrasound system 100. For example, processing circuit 210 may perform calculations and/or operations related to producing an image from signals and or data provided by ultrasound equipment, running an operating system for portable ultrasound system 100, receiving user inputs, etc. Processing circuit 210 may include memory 212 and processor 214 for use in processing tasks. For example, processing circuit 210 may perform calculations and/or operations.

Processor 214 may be, or may include, one or more microprocessors, application specific integrated circuits (ASICs), circuits containing one or more processing components, a group of distributed processing components, circuitry for supporting a microprocessor, or other hardware configured for processing. Processor 214 is configured to execute computer code. The computer code may be stored in memory 212 to complete and facilitate the activities described herein with respect to portable ultrasound system 100. In other embodiments, the computer code may be retrieved and provided to processor 214 from hard disk storage 220 or communications interface 222 (e.g., the computer code may be provided from a source external to main circuit board 200).

Memory 212 may be any volatile or non-volatile computer-readable storage medium capable of storing data or computer code relating to the activities described herein. For example, memory 212 may include modules which are computer code modules (e.g., executable code, object code, source code, script code, machine code, etc.) configured for execution by processor 214. Memory 212 may include computer executable code related to functions including ultrasound imagining, battery management, handling user inputs, displaying data, transmitting and receiving data using a wireless communication device, etc. In some embodiments, processing circuit 210 may represent a collection of multiple processing devices (e.g., multiple processors, etc.). In such cases, processor 214 represents the collective processors of the devices and memory 212 represents the collective storage devices of the devices. When executed by processor 214, processing circuit 210 is configured to complete the activities described herein as associated with portable ultrasound system 100.

Hard disk storage 220 may be a part of memory 212 and/or used for non-volatile long term storage in portable ultrasound system 100. Hard disk storage 220 may store local files, temporary files, ultrasound images, patient data, an operating system, executable code, and any other data for supporting the activities of portable ultrasound device 100 described herein. In some embodiments, hard disk storage 220 is embedded on main circuit board 200. In other embodiments, hard disk storage 220 is located remote from main circuit board 200 and coupled thereto to allow for the transfer of data, electrical power, and/or control signals. Hard disk storage 220 may be an optical drive, magnetic drive, a solid state hard drive, flash memory, etc.

In some embodiments, main circuit board 200 includes communications interface 222. Communications interface 222 may include connections which enable communication between components of main circuit board 200 and communications hardware. For example, communications interface 222 may provide a connection between main circuit board 200 and a network device (e.g., a network card, a wireless transmitter/receiver, etc.). In further embodiments, communications interface 222 may include additional circuitry to support the functionality of attached communications hardware or to facilitate the transfer of data between communications hardware and main circuit board 200. In other embodiments, communications interface 222 may be a system on a chip (SOC) or other integrated system which allows for transmission of data and reception of data. In such a case, communications interface 222 may be coupled directly to main circuit board 200 as either a removable package or embedded package.

Some embodiments of portable ultrasound system 100 include power supply board 224. Power supply board 224 includes components and circuitry for delivering power to components and devices within and/or attached to portable ultrasound system 100. In some embodiments, power supply board 224 includes components for alternating current and direct current conversion, for transforming voltage, for delivering a steady power supply, etc. These components may include transformers, capacitors, modulators, etc. to perform the above functions. In further embodiments, power supply board 224 includes circuitry for determining the available power of a battery power source. In other embodiments, power supply board 224 may receive information regarding the available power of a battery power source from circuitry located remote from power supply board 224. For example, this circuitry may be included within a battery. In some embodiments, power supply board 224 includes circuitry for switching between power sources. For example, power supply board 224 may draw power from a backup battery while a main battery is switched. In further embodiments, power supply board 224 includes circuitry to operate as an uninterruptable power supply in conjunction with a backup battery. Power supply board 224 also includes a connection to main circuit board 200. This connection may allow power supply board 224 to send and receive information from main circuit board 200. For example, power supply board 224 may send information to main circuit board 200 allowing for the determination of remaining battery power. The connection to main circuit board 200 may also allow main circuit board 200 to send commands to power supply board 224. For example, main circuit board 200 may send a command to power supply board 224 to switch from source of power to another (e.g., to switch to a backup battery while a main battery is switched). In some embodiments, power supply board 224 is configured to be a module. In such cases, power supply board 224 may be configured so as to be a replaceable and/or upgradable module. In some embodiments, power supply board 224 is or includes a power supply unit. The power supply unit may convert AC power to DC power for use in portable ultrasound system 100. The power supply may perform additional functions such as short circuit protection, overload protection, undervoltage protection, etc. The power supply may conform to ATX specification. In other embodiments, one or more of the above described functions may be carried out by main circuit board 200.

Main circuit board 200 may also include power supply interface 226 which facilitates the above described communication between power supply board 224 and main circuit board 200. Power supply interface 226 may include connections which enable communication between components of main circuit board 200 and power supply board 224. In further embodiments, power supply interface 226 includes additional circuitry to support the functionality of power supply board 224. For example, power supply interface 226 may include circuitry to facilitate the calculation of remaining battery power, manage switching between available power sources, etc. In other embodiments, the above described functions of power supply board 224 may be carried out by power supply interface 226. For example, power supply interface 226 may be a SOC or other integrated system. In such a case, power supply interface 226 may be coupled directly to main circuit board 200 as either a removable package or embedded package.

With continued reference to FIG. 2, some embodiments of main circuit board 200 include user input interface 228. User input interface 228 may include connections which enable communication between components of main circuit board 200 and user input device hardware. For example, user input interface 228 may provide a connection between main circuit board 200 and a capacitive touchscreen, resistive touchscreen, mouse, keyboard, buttons, and/or a controller for the proceeding. In one embodiment, user input interface 228 couples controllers for touchpad 170, touchscreen 180, and main screen 190 to main circuit board 200. In other embodiments, user input interface 228 includes controller circuitry for touchpad 170, touchscreen 180, and main screen 190. In some embodiments, main circuit board 200 includes a plurality of user input interfaces 228. For example, each user input interface 228 may be associated with a single input device (e.g., touchpad 170, touchscreen 180, a keyboard, buttons, etc.).

In further embodiments, user input interface 228 may include additional circuitry to support the functionality of attached user input hardware or to facilitate the transfer of data between user input hardware and main circuit board 200. For example, user input interface 228 may include controller circuitry so as to function as a touchscreen controller. User input interface 228 may also include circuitry for controlling haptic feedback devices associated with user input hardware. In other embodiments, user input interface 228 may be a SOC or other integrated system which allows for receiving user inputs or otherwise controlling user input hardware. In such a case, user input interface 228 may be coupled directly to main circuit board 200 as either a removable package or embedded package.

Main circuit board 200 may also include ultrasound board interface 230 which facilitates communication between ultrasound board 232 and main circuit board 200. Ultrasound board interface 230 may include connections which enable communication between components of main circuit board 200 and ultrasound board 232. In further embodiments, ultrasound board interface 230 includes additional circuitry to support the functionality of ultrasound board 232. For example, ultrasound board interface 230 may include circuitry to facilitate the calculation of parameters used in generating an image from ultrasound data provided by ultrasound board 232. In some embodiments, ultrasound board interface 230 is a SOC or other integrated system. In such a case, ultrasound board interface 230 may be coupled directly to main circuit board 200 as either a removable package or embedded package.

In other embodiments, ultrasound board interface 230 includes connections which facilitate use of a modular ultrasound board 232. Ultrasound board 232 may be a module (e.g., ultrasound module) capable of performing functions related to ultrasound imaging (e.g., multiplexing sensor signals from an ultrasound probe/transducer, controlling the frequency of ultrasonic waves produced by an ultrasound probe/transducer, etc.). The connections of ultrasound board interface 230 may facilitate replacement of ultrasound board 232 (e.g., to replace ultrasound board 232 with an upgraded board or a board for a different application). For example, ultrasound board interface 230 may include connections which assist in accurately aligning ultrasound board 232 and/or reducing the likelihood of damage to ultrasound board 232 during removal and/or attachment (e.g., by reducing the force required to connect and/or remove the board, by assisting, with a mechanical advantage, the connection and/or removal of the board, etc.).

In embodiments of portable ultrasound system 100 including ultrasound board 232, ultrasound board 232 includes components and circuitry for supporting ultrasound imaging functions of portable ultrasound system 100. In some embodiments, ultrasound board 232 includes integrated circuits, processors, and memory. Ultrasound board 232 may also include one or more transducer/probe socket interfaces 238. Transducer/probe socket interface 238 enables ultrasound transducer/probe 234 (e.g., a probe with a socket type connector) to interface with ultrasound board 232. For example, transducer/probe socket interface 238 may include circuitry and/or hardware connecting ultrasound transducer/probe 234 to ultrasound board 232 for the transfer of electrical power and/or data. Transducer/probe socket interface 238 may include hardware which locks ultrasound transducer/probe 234 into place (e.g., a slot which accepts a pin on ultrasound transducer/probe 234 when ultrasound transducer/probe 234 is rotated). In some embodiments, ultrasound board 232 includes two transducer/probe socket interfaces 238 to allow the connection of two socket type ultrasound transducers/probes 187.

In some embodiments, ultrasound board 232 also includes one or more transducer/probe pin interfaces 236. Transducer/probe pin interface 236 enables an ultrasound transducer/probe 234 with a pin type connector to interface with ultrasound board 232. Transducer/probe pin interface 236 may include circuitry and/or hardware connecting ultrasound transducer/probe 234 to ultrasound board 232 for the transfer of electrical power and/or data. Transducer/probe pin interface 236 may include hardware which locks ultrasound transducer/probe 234 into place. In some embodiments, ultrasound transducer/probe 234 is locked into place with locking lever system 120. In some embodiments, ultrasound board 232 includes more than one transducer/probe pin interfaces 236 to allow the connection of two or more pin type ultrasound transducers/probes 234. In such cases, portable ultrasound system 100 may include one or more locking lever systems 120. In further embodiments, ultrasound board 232 may include interfaces for additional types of transducer/probe connections.

With continued reference to FIG. 2, some embodiments of main circuit board 200 include display interface 240. Display interface 240 may include connections which enable communication between components of main circuit board 200 and display device hardware. For example, display interface 240 may provide a connection between main circuit board 200 and a liquid crystal display, a plasma display, a cathode ray tube display, a light emitting diode display, and/or a display controller or graphics processing unit for the proceeding or other types of display hardware. In some embodiments, the connection of display hardware to main circuit board 200 by display interface 240 allows a processor or dedicated graphics processing unit on main circuit board 200 to control and/or send data to display hardware. Display interface 240 may be configured to send display data to display device hardware in order to produce an image. In some embodiments, main circuit board 200 includes multiple display interfaces 240 for multiple display devices (e.g., three display interfaces 240 connect three displays to main circuit board 200). In other embodiments, one display interface 240 may connect and/or support multiple displays. In one embodiment, three display interfaces 240 couple touchpad 170, touchscreen 180, and main screen 190 to main circuit board 200.

In further embodiments, display interface 240 may include additional circuitry to support the functionality of attached display hardware or to facilitate the transfer of data between display hardware and main circuit board 200. For example, display interface 240 may include controller circuitry, a graphics processing unit, video display controller, etc. In some embodiments, display interface 240 may be a SOC or other integrated system which allows for displaying images with display hardware or otherwise controlling display hardware. Display interface 240 may be coupled directly to main circuit board 200 as either a removable package or embedded package. Processing circuit 210 in conjunction with one or more display interfaces 240 may display images on one or more of touchpad 170, touchscreen 180, and main screen 190.

Referring back to FIG. 1A, in some embodiments, portable ultrasound system 100 includes one or more pin type ultrasound probe interfaces 122. Pin type ultrasound interface 122 may allow an ultrasound probe to connect to an ultrasound board 232 included in ultrasound system 100. For example, an ultrasound probe connected to pin type ultrasound interface 122 may be connected to ultrasound board 232 via transducer/probe pin interface 236. In some embodiments, pin type ultrasound interface 122 allows communication between components of portable ultrasound system 100 and an ultrasound probe. For example, control signals may be provided to the ultrasound probe 112 (e.g., controlling the ultrasound emissions of the probe) and data may be received by ultrasound system 100 from the probe (e.g., imaging data).

In some embodiments, ultrasound system 100 may include locking lever system 120 for securing an ultrasound probe. For example, an ultrasound probe may be secured in pin type ultrasound probe interface 122 by locking lever system 120.

In further embodiments, ultrasound system 100 includes one or more socket type ultrasound probe interfaces 124. Socket type ultrasound probe interfaces 124 may allow a socket type ultrasound probe to connect to an ultrasound board 232 included in ultrasound system 100. For example, an ultrasound probe connected to socket type ultrasound probe interface 124 may be connected to ultrasound board 232 via transducer/probe socket interface 238. In some embodiments, socket type ultrasound probe interface 124 allows communication between components of portable ultrasound system 100 and other components included in or connected with portable ultrasound system 100. For example, control signals may be provided to an ultrasound probe (e.g., controlling the ultrasound emissions of the probe) and data may be received by ultrasound system 100 from the probe (e.g., imaging data).

Figure 3:
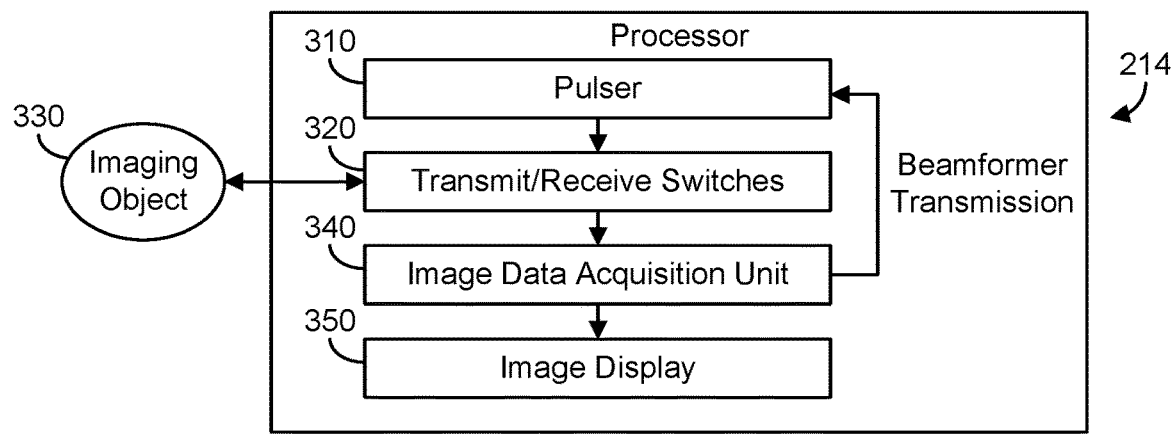
FIG. 3 is a block diagram illustrating a processor of the portable ultrasound system of FIG. 2.

Referring now to FIG. 3, a block diagram illustrating processor 214 is shown, according to an exemplary embodiment. Processor 214 may include a pulser 310, transmit/receive switches 320, an image data acquisition unit 340, and an image display 350 and communicates with an imaging object 330.

Pulser 310 provides the electrical voltage required for excitation of the piezoelectric transducer elements in transducer assembly 102. Pulser 310 may control the output transmit power by adjusting the electrical voltage. In a system that includes a beamformer, the amplitude of the voltage output by pulser 310 may be determined by a digital to analog converter. If the amplitude of the voltage output by pulser 310 is increased, the ultrasound waves transmitted have a higher intensity and echo detection from weaker reflectors may be improved. In another embodiment, the pulser 310 may have a low power setting for obstetric imaging to reduce the power deposited into a fetus. Pulser 310 may provide varied electrical pulses across different channel. In another embodiment, pulser 310 may provide timing delays across different channels.

Transmit/receive switches 320 may be synchronized with pulser 310. The transmit/receive switches 320 may be configured to isolate high voltage associated with pulsing from sensitive amplification stages during the receive mode. The receive mode collects the induced voltages caused by the returning echoes, which consist of a much lower amplitude than the voltages for transmission.

Imaging object 330 may be a patient, a phantom, or other object to receive imaging. The imaging for the patient may take place for diagnostic examination (e.g., an abdominal, an obstetric and gynecological, a cardiac, a pediatric, a musculoskeletal, etc.), research or training.

Image data acquisition unit 340 is discussed in detail with reference to FIG. 4.

Image display 350 receives information from a scan converter and may project the image onto main screen 190, or other display interface. Once the image is displayed, the user input interface 228 may be used to make adjustments to the image to improve image quality. The quality and resolution of the image may be limited by the main screen 190 settings. Zoom features may be available to improve the image being displayed. Two types of zoom features that are commonly used are "read" and "write" zoom. Read zoom enlarges a user defined region of the image and expands the stored information over a larger number of pixels. While the image gets enlarged, the resolution does not change. In contrast, write zoom requires the selected area to be rescanned. The transducer assembly 102 only scans the selected area, and only echoes within the region are acquired.

Figure 4:
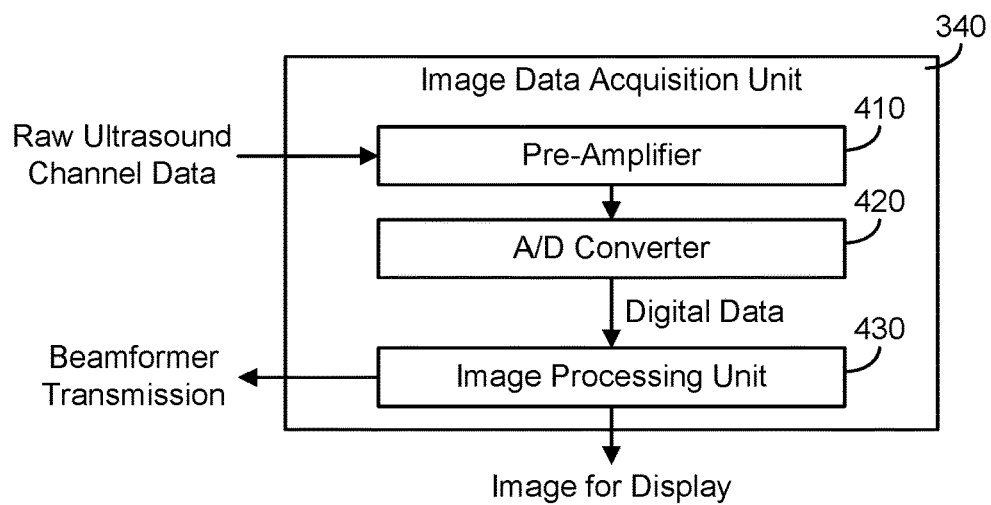
FIG. 4 is a block diagram illustrating an image data acquisition unit of the processor of FIG. 3, according to an exemplary embodiment.

Referring now to FIG. 4, a block diagram illustrating image data acquisition unit 340 of the processor 214 is shown, according to an exemplary embodiment. Pre-amplifier 410 may receive the detected signal voltages from the raw ultrasound data, and amplifies the voltages to useful signal levels. In another embodiment, each piezoelectric element in the ultrasound assembly 100 has its own pre-amplifier 410. The amplified data may be transmitted to the analog to digital (A/D) converter 420, which takes the analog data and coverts it to digital data. In another embodiment, each piezoelectric element in the ultrasound assembly 100 has its own A/D converter 420. In other embodiments, the per-amplifier 410 and A/D converter 420 can run in parallel. The A/D converter 420 may transmit the digital data to the imaging processing unit 430, which is discussed in detail in regard to FIG. 5.

Figure 5:
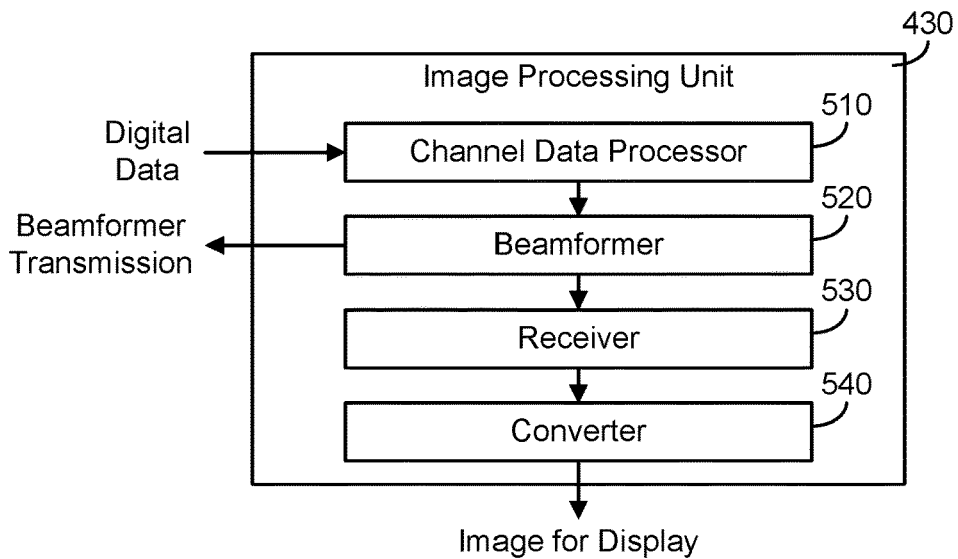
FIG. 5 is a block diagram illustrating an image processing unit of the image data acquisition unit of FIG. 4, according to an exemplary embodiment.

Referring now to FIG. 5, a block diagram illustrating image processing unit 430 of the image data acquisition unit 340 is shown, according to an exemplary embodiment. The digital data transmitted from A/D converter 420 is received by a channel data processor 510, which will be discussed in detail with regard to FIG. 6A-6B. The processed channel data may be transmitted to a beamformer 520.

Beamformer 520 may generate the electronic delay for individual transducer elements in an array. This causes transmit and receiving focus, which, in a phased array, causes beam steering to occur. In another embodiment, the beamformer 520 may be a digital beamformer.

Receiver 530 may receive data from the beamformer 520, which may represent echo information as a function of time, which corresponds to depth. The receiver 530 may be configured to conduct further processing. The processing done by receiver 530 may include gain adjustments and dynamic frequency tuning, dynamic range compression, rectification, demodulation, and envelope detection, rejection, and processed images.

Gain adjustments may be user-adjustable amplification settings for the returning echo signals as a function of time, which further compensation for beam attenuation. Gain adjustments may be varied based on the particular application of the ultrasound system 100. In general, the ideal gain adjustments make all equally reflective boundaries equal amplitude, regardless of the depth.

Dynamic frequency tuning involves changing the sensitivity of a tuner bandwidth with time. This may result in echoes from shallower depths to be tuned to a higher frequency. In another embodiment, echoes from a deeper depths are tuned to a lower frequency. Dynamic frequency tuning may be conducted to accommodate for the increased attenuation with respect to depth.

Dynamic range compression defines the operational range of an electronic device from a threshold level to a saturation level. Signal ranges may be reduced to allow accurate display images. In some embodiments, the dynamic range compression is done in analog. In other embodiments, the dynamic range compression is done in digital.

Rectification inverts negative echo signals to positive echo signals. Demodulation and envelope detection convert rectified amplitudes into a smoothed, single pulse. Rejection may allow for thresholds to be set by the user for digitizing. Only signal data with amplitudes higher than the threshold will be digitized. Rejection may remove low-level noise and sound scattered by the electronics. Processed images are optimized for gray-scale or color ranges so no further adjustments are needed. The receiver 530 may transmit the processed data to converter 540.

Converter 540 creates the image from the echo information from distinct beam directions. The converter 540 may also perform scan conversion which enables the image data to be viewed on main screen 190 because the image acquisition and display may have different formats. In some embodiments, digital data from the converter 540 is transmitted to a scan converter memory. The scan converter memory may be configured as a matrix, where each pixel has a memory address that distinctly distinguishes its location. During image acquisition, the digital signals are placed into the memory address that corresponds to the relative reflector position in the transducer probe 112, as close as possible. The transducer beam, orientation, and echo delay times may determine the memory address where the information may be stored. Converter 540 may transmit the data for the image display.

Figure 6A:
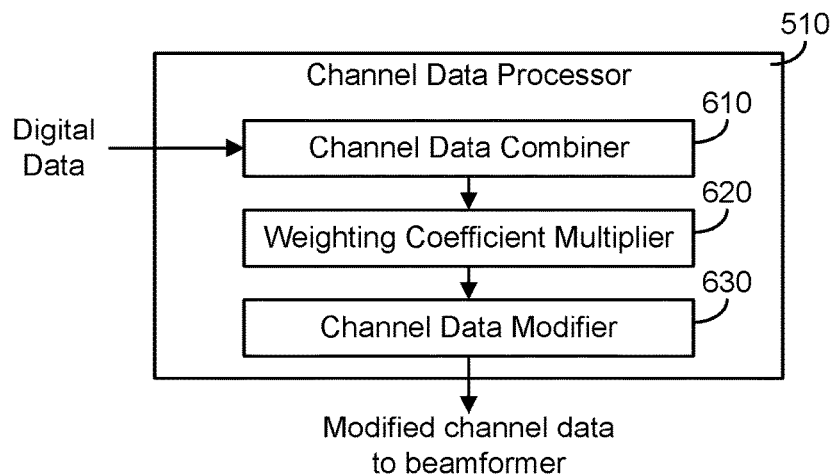
FIGS. 6A-6B are block diagrams illustrating a channel data processor of the image processing unit of FIG. 5 in greater detail, according to exemplary embodiments.

Referring now to FIG. 6A, a block diagram illustrating channel data processor 510 of the image processing unit 430 in greater detail, according to an exemplary embodiment. The channel data processor 510 may include a channel data combiner 610, a weighting coefficient multiplier 620, and a channel data modifier 630. While these elements are shown to occur sequentially, they may occur in parallel, or in a different sequence, depending on the embodiment.

The digital data from A/D converter 420 may be received by a channel data combiner 610. In one embodiment, the received digital data is IQ/RF data. The channel data combiner 610 combines the digital channel data into a single value representative of all the individual channel data. In an exemplary embodiment, the channel data combiner 610 may average the data across the channels for every transmit event. In another embodiment, the channel data combiner 610 may combine the channel data in another mathematical or statistical manner. The channel data combiner 610 may only combine selected channels. These channels may be selected if noise is only occurring on certain channels and noise is estimated on those channels, causing only those channels to be used by the channel data combiner 610. In some embodiments, the channel data combiner 610 may select the channels based on the type of noise. In another embodiment, the channel data combiner 610 may select channels to include based on the origin of the noise. The channel data combiner 610 may combine channel data based on a function of one or more of the following: time of a transmit event, depth of a spatial dimension in range, and/or channel of spatial dimension in azimuth. The channel data combiner 610 may transmit the combined channel data to a weighting coefficient multiplier 620.

Weighting coefficient multiplier 620 may receive the combined channel data from channel data combiner 610 and multiply the combined channel data by a weighting coefficient. The weighting coefficient may change adaptively based on the channel data, providing adaptive noise reduction. In one embodiment, the weighting coefficient may be based on spatial distribution. In another embodiment, the weighting coefficient may be based on spatial location. In yet another embodiment, the weighting coefficient may be based on a lookup table reference. The weighting coefficient may be based on a function of combined elements. The weighting coefficient may be based on a user defined function. The user defined function may be based on learned knowledge and be made for specific transmit adaptations. The weighting coefficient multiplier 620 may transmit the multiplied combined channel data to the channel data modifier 630.

The channel data modifier 630 modifies the individual channel data based on the multiplied combined channel data. The channel data modifier 630 may take the multiplied combined channel data and subtract it from the original channel data, for every selected channel. Subtraction is performed if the noise is additive, so by removing the multiplied combined channel data from the original channel data, common mode noise is suppressed. In another embodiment, channel data modifier 630 may take the multiplied combined channel data and divide the original channel data by the multiplied combined channel data, for every selected channel. Division is performed if the noise is multiplicative, so by removing the multiplied combined channel data from the original channel data, common mode noise is suppressed. The channel data modifier 630 may transmit the modified channel data to the beamformer 520. By combining and modifying the channel data prior to beamforming, the common mode noise is suppressed before beamforming adjusts the steering and before further processing is performed. The beamformer 520 may send data causing transmitting and receiving focus to the pulser 310, which, in a phased array, causes beam steering to occur. Image quality is enhanced by performing channel data processing prior to beamforming because the data received by the beamformer 520 has suppressed common mode noise, as opposed to suppressing the noise after beamforming. By suppressing the common mode noise, the information that the beamformer 520 bases its beam steering on is more focused and accurate. With enhanced beam steering, the image quality is enhanced. In some embodiments, the data transmitted from the channel data processor 510 is used to determine which channels, if any, should be removed from use in subsequent processing through feedback via the beamformer 520, altering transmit.

Figure 6B:
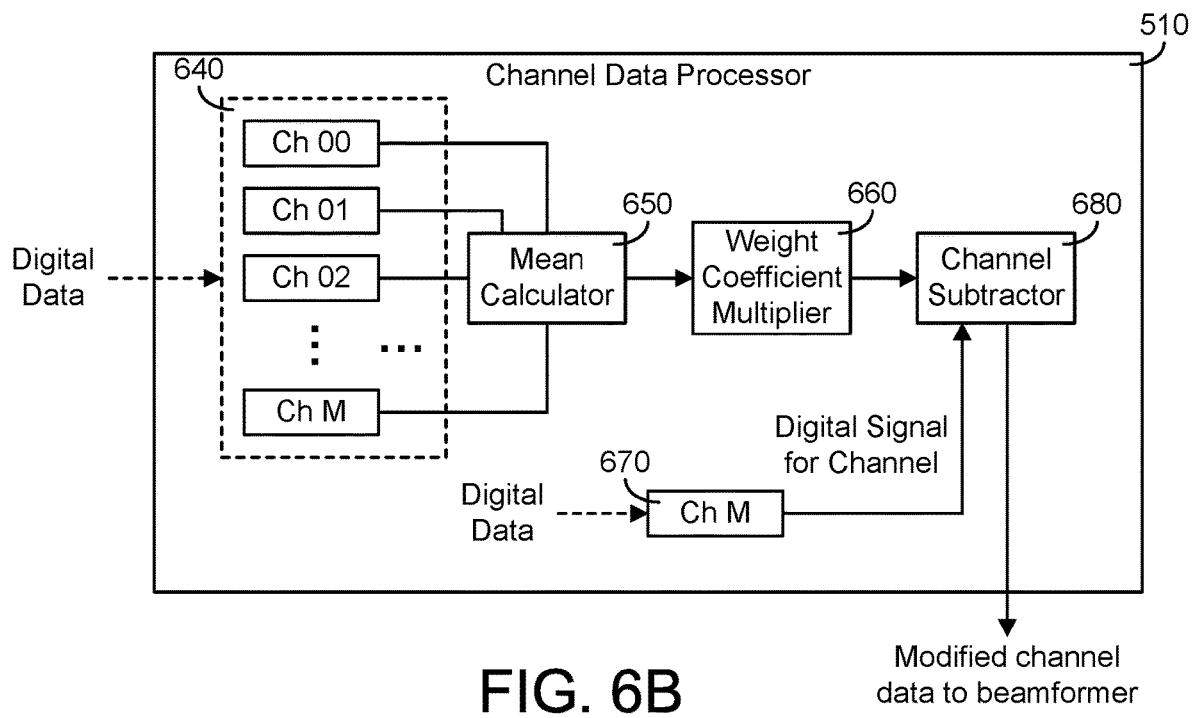

Referring now to FIG. 6B, a block diagram illustrating an exemplary embodiment of channel data processor 510 of the image processing unit 430 greater detail. The channel data processor 510 includes channel data 640, mean calculator 650, weight coefficient multiplier 660, channel subtractor 680 and original channel data 670. The digital data is received by the channel data processor 510, the digital data enters as channel data 640. Each channel has separate data that is being received. The channel data 640 may be transmitted to mean calculator 650.

Mean calculator 650 may combine the channel data 640 to reduce the common mode noise. The mean calculator 650 may calculate an arithmetic mean. The mean calculator 650 may transmit the combined channel data to weight coefficient multiplier 660. The weight coefficient multiplier 660 multiplies the combined channel data by a weight coefficient. The weighting coefficient may change adaptively based on the channel data, providing adaptive noise reduction. In one embodiment, the weighting coefficient may be based on spatial distribution. In another embodiment, the weighting coefficient may be based on spatial location. In yet another embodiment, the weighting coefficient may be based on a lookup table reference. The weighting coefficient may be based on a function of combined elements. The weighting coefficient may be based on a user defined function. The user defined function may be based on learned knowledge and be made for specific transmit adaptations. The weighting coefficient multiplier 660 may transmit the multiplied combined channel data to the channel subtractor 680.

Channel subtractor 680 may receive the multiplied combined channel data from the weight coefficient multiplier 660. The channel subtractor 680 may receive the original digital channel data 670. The channel subtractor 680 may take the multiplied combined channel data and subtract it from the original channel data 670. The channel subtractor 680 may transmit modified channel data. In an exemplary embodiment, modified channel data is received by beamformer 520.

Referring now to FIGS. 6A and 6B, the channel data processor 510 may have processing electronics to implement the following equation for channel data processing.

$$ModChData(r, i) = ChData(r, i) - \alpha(r) \cdot \frac{\sum_{k=1}^{k=N} ChData(r, k)}{N}$$

$$\text{where } \alpha(r) = c \cdot \frac{r}{r_{max}}$$

where ChData(r,i) is the channel data, ModChData(r,i) is the modified channel data, r is the range, i is the channel of interest, k is the selected channel for iteration in the summation, N is the number of channels, and α(r) represents the weighting coefficient, wherein c is a constant and $r_{max}$ is the maximum range for the channel's transmit frequency. In another embodiment, the processing electronics are configured to implement the following equation for channel data processing.

$$ModChData(r, i, t) =$$

$$\begin{cases} ChData(r, i, t) - \alpha(r, i, t) \cdot \\ \quad \frac{\sum_{k=A}^{k=B} ChData(r, k, t)}{N}, & \text{Noise is additive} \\ ChData(r, i, t) \div \\ \quad \left( \alpha(r, i, t) \cdot \frac{\sum_{k=A}^{k=B} ChData(r, k, t)}{N} \right), & \text{Noise is multiplicative} \end{cases}$$

where $\alpha(r, i, t) = \text{Function}(r, i, t)$ where ChData(r,i) is the channel data, ModChData(r,i,t) is the modified channel data, r is the range, i is the channel of interest, k is the selected channel for iteration in the summation, N is the number of channels, t is the time, A and B are the bounds of summation, which can a subset of the channels in the channel data, and α(r,i,t) represents the weighting coefficient, which can be a function that varies based on the operations of the ultrasound system 100. In another embodiment, the processing electronics are configured to implement the following equation for channel data processing.

$$ModChData(r, i, t) =$$

$$\begin{cases} ChData(r, i, t, l) - \alpha(r, i, t) \cdot \\ \quad \frac{\sum_{t=Tst}^{t=TEnd} \sum_{l=Lst}^{l=Lend} \sum_{k=A}^{k=B} ChData(r, k, t, l)}{N}, & \text{Noise is additive} \\ ChData(r, i, t, l) \div \\ \quad \left( \frac{\alpha(r, i, t) \cdot \sum_{t=Tst}^{t=TEnd} \sum_{l=Lst}^{l=Lend} \sum_{k=A}^{k=B} ChData(r, k, t, l)}{N} \right), & \text{Noise is multiplicative} \end{cases}$$

where $\alpha(r, i, t) = \text{Function}(r, i, t)$ where ChData(r,i,t,l) is the channel data, ModChData(r, i,t,l) is the modified channel data, r is the range, i is the channel of interest, k is the selected channel for iteration in the summation, N is the number of channels, t is the time (where TSt is a starting time and TEnd is an ending time for summation), l is the lateral dimensions (where LSt is a starting lateral position of the channel data and Lend is an ending lateral position over which to average), A and B are the bounds of channels for the summation which can be a subset of the channels in the channel data, and $\alpha(r,i,t)$ represents the weighting coefficient, which can be a function that varies based on the operations of the ultrasound system 100. Note in the above equations, the number of channels used for noise estimation is arbitrary and depends on the type and origin of noise. For systems that have noise on certain channels, noise is estimated on those channels and the method is applied only on those channels. In addition, the weighting coefficient function could be a reference lookup table.

In other embodiments, the weighting coefficient function may be different for different channels. In another embodiment, the weighting coefficient function may change adaptively based on the channel data. The weighting coefficient may be based on a user defined function. The user defined function may be based on learned knowledge and be made for specific transmit adaptations.

Figure 7:
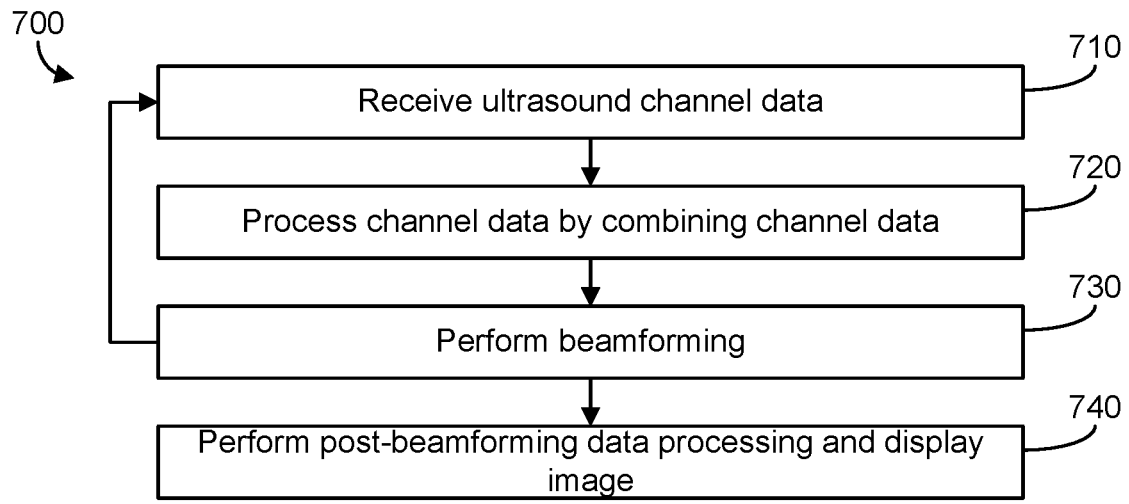
FIG. 7 is a flowchart of a process for processing channel data in an ultrasound system, according to an exemplary embodiment.

Referring now to FIG. 7, a flowchart of a process 700 for processing channel data in an ultrasound system is shown, according to an exemplary embodiment. In various embodiments, process 700 may be performed by processing electronics of ultrasound system 100. In other embodiments, process 700 may be performed by software accompanied by ultrasound system 100. Advantageously, process 700 suppresses common mode noise prior to beamforming. By suppressing common mode noise, the ultrasound system 100 has lower interference noise from external sources, improved tolerance to variations in the analog ultrasound components and transducers, improved imaging modes especially Doppler modes, and reduced system costs.

The process for processing channel data 700 may start with the receiving of ultrasound channel data 710. The channel data may be received as digital or analog data. In another embodiment, channel data is IQ/RF data. In some embodiments, ultrasound channel data is received from an A/D converter. The data being received may have been pre-processed. In another embodiment, the data received may not have had any pre-processing. The next step in the process for processing channel data 700 is processing channel data by combining channel data 720. More detailed means of combining channel data can be seen in reference to FIG. 8. In some embodiments, combing channel data 720 is performed by channel data processor 510.

The next step in the process for processing channel data 700 is performing beamforming 730. In some embodiments, beamforming is done by beamformer 520. Beamforming 720 may be signal processing that is used for directional transmission and or reception of transducer assembly 102 or probe 112. The processed data obtained after completing beamforming 720 may then be used to modify the data that is being received by changing the data being collected.

The final step in process 700 is to perform post-beamforming data processing and display the image 740. The data processing after the beamforming may be done by receiver 530 and converter 540. The post processing that takes place may include gain adjustments and dynamic frequency tuning, dynamic range compression, rectification, demodulation, and envelope detection, rejection, and processed images. These processing techniques were discussed with reference to FIG. 5. The processed data may be transformed to allow an image to be displayed. The image could be displayed on main screen 190.

Figure 8:
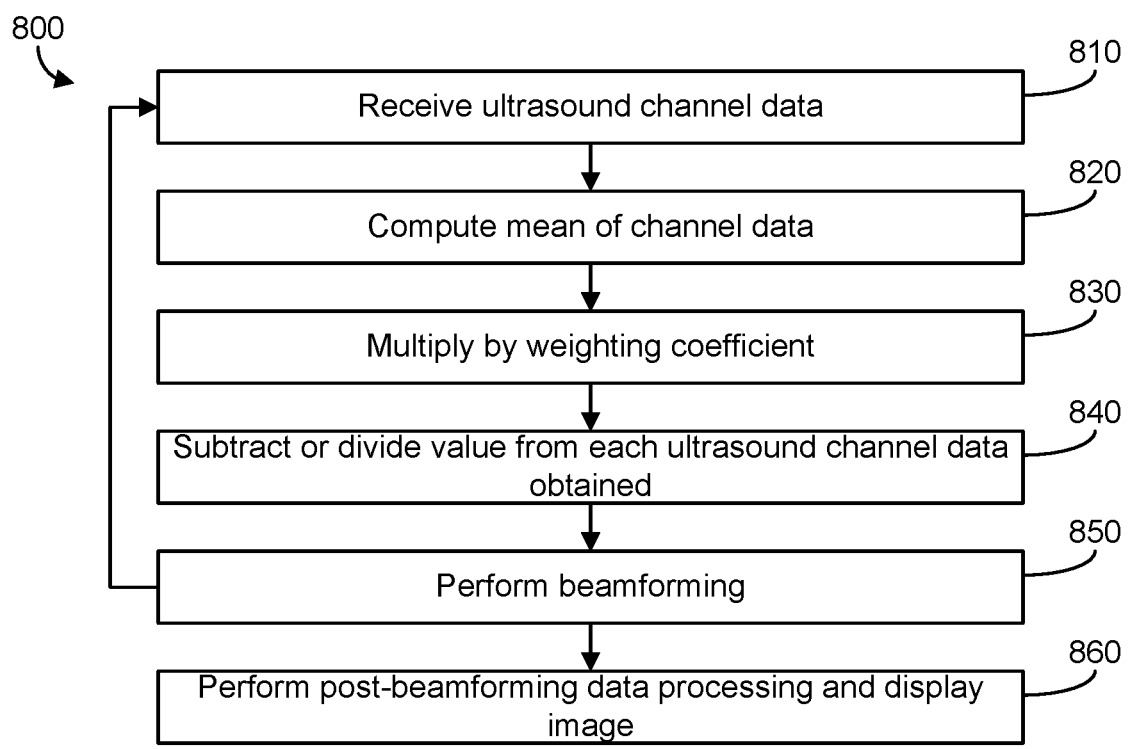
FIG. 8 is a flowchart of a process for processing channel data in an ultrasound system, shown in greater detail, according to an exemplary embodiment.

Referring now to FIG. 8, a flowchart of a process 800 for processing channel data in an ultrasound system, shown in greater detail is shown, according to an exemplary embodiment. In various embodiments, process 800 may be performed by processing electronics of ultrasound system 100. In other embodiments, process 800 may be performed by software accompanied by ultrasound system 100. Advantageously, process 800 suppresses common mode noise prior to beamforming. By suppressing common mode noise, the ultrasound system 100 has lower interference noise from external sources, improved tolerance to variations in the analog ultrasound components and transducers, improved imaging modes especially Doppler modes, and reduced system costs.

The process for processing channel data 800 starts with the receiving of ultrasound channel data 810. The channel data may be received as digital or analog data. In another embodiment, channel data is IQ/RF data. In some embodiments, ultrasound channel data is received from an A/D converter. The data being received may have been pre-processed. In another embodiment, the data received may not have had any pre-processing. The next step in the process 800 for processing channel data is to compute the mean of channel data 820. In some embodiments, computing the mean of channel data 820 may be done by combiner 610. In another embodiment, computing the mean of channel data 650 may be done by mean calculator 650. The computing of the mean of channel data 820 may be an arithmetic mean.

The next step the process 800 for processing channel data is to multiply by weighting coefficient 830. The weighting coefficient may change adaptively based on the channel data, providing adaptive noise reduction. In one embodiment, the weighting coefficient may be based on spatial distribution. In another embodiment, the weighting coefficient may be based on spatial location. In yet another embodiment, the weighting coefficient may be based on a lookup table reference. The weighting coefficient may be based on a function of combined elements. The weighting coefficient may be based on a user defined function. The user defined function may be based on learned knowledge and be made for specific transmit adaptations. Multiplying by weighting coefficient 830 may be done by weighting coefficient multiplier 620.

The next step in the process 800 for processing channel data is subtracting or dividing the value from each ultrasound channel data 840 obtained after multiplying be weighting coefficient in step 630. In another embodiment, channel data modifier 630 may perform step 840. Step 840 may be conducted only for selected channels. Subtraction is performed if the noise is additive, so by removing the multiplied combined channel data from the original channel data, common mode noise is suppressed. Division is performed if the noise is multiplicative, so by removing the multiplied combined channel data from the original channel data, common mode noise is suppressed. By combining and modifying the channel data prior to beamforming, the common mode noise is suppressed before repeating the process. The beamformer 520 may send data causing transmitting and receiving focus to the pulser 310, which, in a phased array, causes beam steering to occur. Image quality is enhanced by performing channel data processing prior to beamforming because the data received by the beamformer 520 has suppressed common mode noise. By suppressing the common mode noise, the information that the beamformer 520 bases its beam steering on is more focused and accurate. With enhanced beam steering, the image quality is enhanced. In some embodiments, the data transmitted from the channel data processor 510 is used to determine which channels, if any, should be removed from use in subsequent processing through feedback via beamformer 520, altering transmit.

The next step in the process 800 for processing channel data is performing beamforming 850. In some embodiments, beamforming is done by beamformer 520. Beamforming 850 may be a signal processing that is used for directional transmission and or reception of transducer assembly 102 or probe 112. The processed data obtained after completing beamforming 850 may then be used to modify the data received by changing the data collected.

The final step in process 800 may be to perform post-beamforming data processing and display the image 860. The data processing after the beamforming may be done by receiver 530 and converter 540. The post processing that takes place may include gain adjustments and dynamic frequency tuning, dynamic range compression, rectification, demodulation, and envelope detection, rejection, and processed images. These processing techniques were discussed with reference to FIG. 5. The processed data may then be transformed to allow an image to be displayed. The image could be displayed on main screen 190.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. An ultrasound processing system, comprising:

an ultrasound interface that receives ultrasound imaging information; and processing electronics coupled to the ultrasound interface and configured to utilize the ultrasound imaging information to perform processing across a plurality of ultrasound channels by:

selecting channels from the plurality of ultrasound channels to be combined based on at least one of: a type of noise in the channels, an origin of the noise in the channels, a function of time of a transmit event in the channels, a function of depth of a spatial dimension in range in the channels, and a spatial dimension in azimuth of the channels;

combining digital ultrasound channel data of the selected channels of the ultrasound imaging information prior to beamforming, the digital ultrasound channel data corresponding to a transmit event;

generating weighted ultrasound channel data by applying a weighting coefficient to the combined digital ultrasound channel data;

generating modified ultrasound channel data for each of the selected channels for adaptively reducing common mode noise of the digital ultrasound channel data from the selected channels by (i) applying a first operation to the digital ultrasound channel data using the weighted ultrasound channel data based on the common mode noise being additive noise or (ii) applying a second operation to the digital ultrasound channel data using the weighted ultrasound channel data based on the common mode noise being multiplicative noise;

and providing the modified ultrasound channel data to a beamformer.

2. The ultrasound processing system of claim 1, wherein the processing electronics combine the digital ultrasound channel data by obtaining an arithmetic mean.

3. The ultrasound processing system of claim 1, wherein the processing electronics combine the digital ultrasound channel data adaptively as a function of time of a transmit event.

4. The ultrasound processing system of claim 1, wherein the processing electronics combine the digital ultrasound channel data adaptively as a function of depth of a spatial dimension in range.

5. The ultrasound processing system of claim 1, wherein the processing electronics combine the digital ultrasound channel data adaptively as a function of a channel of spatial dimension in azimuth.

6. The ultrasound processing system of claim 1, wherein the processing electronics combine the digital ultrasound channel data adaptively as a function of a combination of elements.

7. The ultrasound processing system of claim 1, wherein the weighting coefficients are based on spatial distribution.

8. The ultrasound processing system of claim 1, wherein the weighting coefficient is based on a function of combined elements.

9. The ultrasound processing system of claim 1, wherein the processing electronics remove digital ultrasound channel data multiplied by the weighting coefficient from the digital ultrasound channel data to generate the modified ultrasound channel data.

10. The ultrasound processing system of claim 1, wherein the processing electronics use the modified ultrasound channel data to determine which channels to eliminate from user.

11. An ultrasound processing system, comprising:

an ultrasound interface that receives ultrasound imaging information; and processing electronics coupled to the ultrasound interface and configured to utilize the ultrasound imaging information to perform processing across a plurality of ultrasound channels by:

selecting a channels from the plurality of ultrasound channels to be combined based on at least one of: a type of noise in the channels, an origin of the noise in the channels, a function of time of a transmit event in the channels, a function of depth of a spatial dimension in range in the channels, and a spatial dimension in azimuth of the channels;

combining digital ultrasound channel data of the selected channels of the ultrasound imaging information prior to beamforming, the digital ultrasound channel data corresponding to a transmit event;

generating weighted ultrasound channel data by applying a weighting coefficient to the combined digital ultrasound channel data;

generating modified ultrasound channel data for each of the selected channels for adaptively reducing common mode noise of the digital ultrasound channel data from the selected channels by (i) applying a first operation to the digital ultrasound channel data using the weighted ultrasound channel data based on the common mode noise being additive noise or (ii) applying a second operation to the digital ultrasound channel data using the weighted ultrasound channel data based on the common mode noise being multiplicative noise; and providing the modified ultrasound channel data to a beamformer.

* * * * *